United States Patent
Kim et al.

(10) Patent No.: US 11,154,580 B1
(45) Date of Patent: Oct. 26, 2021

(54) COMPOSITION FOR PREVENTING, AMELIORATING OR TREATING ACNE SYMPTOMS USING NATURAL EXTRACTS AS ACTIVE INGREDIENTS

(71) Applicant: CELIM BIOTECH Co.Ltd, Yangsan-si (KR)

(72) Inventors: Jun Wan Kim, Busan (KR); Yeong Cheol Park, Gimje-si (KR); Kyung Ho Lee, Goyang-si (KR); Hyungwoo Kim, Yangsan-si (KR)

(73) Assignee: CELIM BIOTECH CO.LTD, Yangsan-si (KR)

( * ) Notice: Subject to any disclaimer, the term of this patent is extended or adjusted under 35 U.S.C. 154(b) by 0 days.

(21) Appl. No.: 17/197,998

(22) Filed: Mar. 10, 2021

(30) Foreign Application Priority Data

Apr. 10, 2020 (KR) .................. 10-2020-0044123

(51) Int. Cl.
| | |
|---|---|
| *A61K 36/00* | (2006.01) |
| *A61K 36/185* | (2006.01) |
| *A61K 36/49* | (2006.01) |
| *A61K 36/78* | (2006.01) |
| *A61P 17/10* | (2006.01) |
| *A61K 36/14* | (2006.01) |
| *A61K 9/14* | (2006.01) |
| *A61K 36/28* | (2006.01) |

(52) U.S. Cl.
CPC ............ *A61K 36/185* (2013.01); *A61K 9/141* (2013.01); *A61K 36/14* (2013.01); *A61K 36/28* (2013.01); *A61K 36/49* (2013.01); *A61K 36/78* (2013.01); *A61P 17/10* (2018.01)

(58) Field of Classification Search
CPC ...................................................... A61K 36/00
USPC ........................................................ 424/725
See application file for complete search history.

(56) References Cited

FOREIGN PATENT DOCUMENTS

| KR | 19950008762 B1 | | 8/1995 |
|---|---|---|---|
| KR | 20060092333 A | | 8/2006 |
| KR | 101661688 | * | 9/2016 |
| KR | 101928096 B1 | | 12/2018 |

* cited by examiner

*Primary Examiner* — Michael V Meller
(74) *Attorney, Agent, or Firm* — STIP Law Group, LLC

(57) ABSTRACT

Proposed is a composition for preventing, ameliorating or treating acne symptoms including a *Sesamum indicum* seed extract, a *Quercus robur* bark extract and a *Houttuynia cordata* extract as active ingredients, and at least one natural substance of a *Cirsium japonicum* extract and *Thuja orientalis* as an additional active ingredient. The composition for preventing, ameliorating or treating acne symptoms contains, as active ingredients, natural extracts having the effects of prevention, amelioration or treatment of acne by exhibiting high antibacterial activity against *C. acnes*, which is a strain causative of acne.

6 Claims, No Drawings

COMPOSITION FOR PREVENTING, AMELIORATING OR TREATING ACNE SYMPTOMS USING NATURAL EXTRACTS AS ACTIVE INGREDIENTS

CROSS-REFERENCE TO RELATED APPLICATIONS

This application claims the priority of the Korean Patent Applications NO 10-2020-0044123 filed on Apr. 10, 2020, in the Korean Intellectual Property Office, the disclosure of which is incorporated herein by reference.

BACKGROUND OF THE DISCLOSURE

1. Technical Field

The present disclosure relates to a composition for preventing, ameliorating or treating acne symptoms using natural extracts as active ingredients, and more particularly to a composition containing, as active ingredients, a *Sesamum indicum* seed extract, a *Quercus robur* bark extract, a *Houttuynia cordata* extract, a *Cirsium japonicum* extract, and a *Thuja orientalis* extract.

2. Description of the Related Art

Acne is a chronic inflammatory skin disease that occurs in the pilosebaceous unit. Acne results from complex interactions between various factors, and is typically known to cause inflammation due to the formation of colonies of *Cutibacterium acnes* (*C. acnes*), which is acne bacteria, in the skin.

*C. acnes* is a gram-positive aerotolerant anaerobe with a slow growth rate, is one of representative microorganisms (Corynebacteria, Staphylococci, Propionibacteria) residing on the skin of healthy adults, and was taxonomically reclassified based on the results of biochemical and genomic studies in 2016, and thus the name was changed from *Propionibacterium acnes* to *Cutibacterium acnes*.

*C. acnes* is less common on the surface of the skin (less than 2% of all resident skin flora), but is dominant in sebaceous follicles. In the case of patients with acne vulgaris, the prevailing theory has been that *C. acnes* proliferates more than in normal persons, but according to a recent report, the distribution of *C. acnes* is almost the same as that of normal skin. For healthy skin, *C. acnes* plays a beneficial role in maintaining skin homeostasis and inhibiting the formation of colonies of other harmful bacteria, but it is known that acne is caused by imbalance of resident skin flora and action of a subtype of *C. acnes*, such as the acne-associated phylotype IA1, as an opportunistic pathogen due to the influence of a hyperseborrheic environment.

*C. acnes*, which is a gram-positive polymorphic *bacillus* that grows under anaerobic conditions, is present in the human skin and produces inflammatory mediators through multinuclear leukocytes, mononuclear leukocytes and macrophages, thereby acting as an acne-causing pathogen and playing a key role in acne mainly occurring near the head and body where the sebaceous glands are active. Most acne patients suffer from non-inflammatory acne, inflammatory papules, pustules, and the like, but severe inflammation may occur in some patients, and may leave scars.

The treatment of such acne is not easy, and acne bacteria exhibiting antibiotic resistance due to prescription of antibiotics for treatment have recently been reported, and it is thus becoming important to find a new antibacterial substance in order to overcome this problem.

Recently, in the pharmaceutical field, the use of chemical-based antibiotics has been reduced, and as an alternative thereto, strategies to market antibacterial agents derived from natural substances have received increased attention.

According to this research trend, many studies have been made on medicinal plants, among various antibacterial resources that control acne bacteria, but the use of natural substances to control acne bacteria is still insufficient.

Therefore, the present disclosure is intended to provide a novel composition for preventing, ameliorating or treating acne symptoms using, as an active ingredient, a natural extract that exhibits antibacterial activity against *C. acnes*, which is acne bacteria.

Below is a description of conventional techniques in the art to which the technology of the present disclosure belongs and of the technical matters that the present disclosure aims to achieve differently than the conventional techniques.

First, Korean Patent Application Publication No. 10-2006-0092333 (Aug. 23, 2006) discloses a cosmetic composition for treating acne, and more specifically a cosmetic composition containing a mixture of sanguinarine, grape seed oil, and *Sesamum indicum* oil, thereby inhibiting the growth of acne-causing bacteria and enabling effective treatment of acne.

In addition, Korean Patent No. 10-1928096 (Publication date: Dec. 13, 2018) discloses a method of preparing a natural herb material composition using a medicinal plant containing an active ingredient that reduces acne or atopy skin disease or improves the skin and a natural herb material composition prepared using the method, the composition having an excellent skin beauty enhancement effect, obtained by extracting and fermenting various medicinal plants containing active ingredients that are effective for skin beauty. More specifically, a composition having an effect of relieving acne and atopy, including leaf-based medicinal plants, including bamboo leaves, *Centella asiatica, Saururus chinensis, Diospyros kaki* Thunb, *Selaginella tamariscina, Camellia sinensis, Portulaca oleracea*, mugwort, *Houttuynia cordata*, pine needles, *Artemisia annua*, thistle, peach leaves and *Duchesnea indica*, is disclosed.

In addition, Korean Patent Application Publication No. 10-1995-0008762 (Laid-open date: Jul. 20, 1993) discloses a cosmetic composition that is effective for acne by inhibiting the growth of *Propionibacterium acnes* (classified as *Cutibacterium* after 2016), by mixing plant extracts obtained from myrrh, *Rhus* semialata gall, *Terminalia chebula, Thuja orientalis* leaves, and ginkgo leaves.

The present applicant has ascertained that, when the composition for preventing and ameliorating acne symptoms using plant extracts includes a combination of specific extracts, among natural plant extracts, the antibacterial activity against acne-causing bacteria may exhibit a synergistic effect, beyond the simple sum of the individual extract activities, thus culminating in the present disclosure.

SUMMARY OF THE DISCLOSURE

The present disclosure has been devised to solve the problems encountered in the related art, and an objective of the present disclosure is to provide a composition for preventing, ameliorating or treating acne symptoms using, as active ingredients, natural extracts having high antibacterial activity against the *C. acnes* strain, which causes acne.

In order to accomplish the above objective, the present disclosure provides a composition for preventing, ameliorating or treating acne symptoms including a *Sesamum indicum* seed extract, a *Quercus robur* bark extract, and a *Houttuynia cordata* extract as active ingredients, and at least one of a *Cirsium japonicum* extract and a *Thuja orientalis* extract as an additional active ingredient.

Here, the *Cirsium japonicum* extract may be an extract extracted from at least one of a flower, leaf, and stem of *Cirsium japonicum*, and the *Thuja orientalis* extract may be an extract extracted from at least one of *Thuja orientalis* sap and a *Thuja orientalis* leaf.

In an embodiment of the present disclosure, each of the *Sesamum indicum* seed extract, the *Quercus robur* bark extract, the *Houttuynia cordata* extract, the *Cirsium japonicum* extract, and the *Thuja orientalis* extract may be used in an amount of 0.05 to 5 parts by weight based on 100 parts by weight of purified water.

In an embodiment of the present disclosure, the composition may further include purified water, vitamin C, royal jelly, glycerin, ethanol, and xanthan gum, in which each of the vitamin C, royal jelly, glycerin, ethanol, and xanthan gum may be used in an amount of 0.01 to 15 parts by weight based on 100 parts by weight of the purified water.

The composition according to the present disclosure may be in a formulation of a powder, a gel, an ointment, a cream, a liquid or an aerosol.

In addition, the present disclosure provides a cosmetic composition for preventing, ameliorating or treating acne symptoms including the composition for preventing, ameliorating or treating acne symptoms described above.

The cosmetic composition may be in any one form selected from the group consisting of a skin lotion, a nourishing lotion, a gel, a water-soluble liquid, a milk lotion, a nourishing cream, a massage cream, an essence, an eye cream, an oil-in-water (O/W) or water-in-oil (W/O) emulsion, an oil dispersion in an aqueous phase using globules, an ointment, a cleansing cream, a cleansing foam, a cleansing water, a pack or body oil, an oil-in-water or water-in-oil makeup base, a foundation, a skin cover, a face powder, and a two-way cake.

According to the present disclosure, a composition for preventing, ameliorating or treating acne symptoms using natural extracts as active ingredients includes a *Sesamum indicum* seed extract, a *Quercus robur* bark extract, and a *Houttuynia cordata* extract as active ingredients, and further includes a *Cirsium japonicum* extract and/or a *Thuja orientalis* extract as additional active ingredients, thus exhibiting antibacterial activity against the *C. acnes* strain, which causes acne in the skin, thereby inhibiting or reducing the expression of acne skin diseases. The components of the composition are natural substances that can be obtained from nature, and a composition prepared using the same has the advantage of avoiding cytotoxicity and side effects on the skin.

DESCRIPTION OF SPECIFIC EMBODIMENTS

Hereinafter, a detailed description will be given of a composition for preventing, ameliorating or treating acne symptoms using natural extracts as active ingredients according to the present disclosure with reference to the accompanying drawings.

According to the present disclosure, the composition for preventing, ameliorating or treating acne symptoms using natural extracts as active ingredients includes a *Sesamum indicum* seed extract, a *Quercus robur* bark extract, and a *Houttuynia cordata* extract as active ingredients, and also includes at least one of a *Cirsium japonicum* extract and *Thuja orientalis* as an additional active ingredient.

For reference, *Sesamum indicum* is a plant of the family Pedaliaceae. It is a 90-150 cm tall annual grass with short hairs and long oval or willow-shaped leaves facing each other. Seeds are collected from August to September when the fruit ripens. Black seeds are used as medicine, and white seeds are used to make oil. Oil is squeezed from dry seeds, and the oil has a light yellow color and a fragrant odor. The seeds contain 54-60% oil, 21% protein, 16% water-soluble carbohydrates, 5% ash and other lecithins, histidine, tryptophan, phytin, choline and the like. The oil is glycerides of oleic acid (48.1%), linoleic acid (36.8%), palmitic acid (77%), stearic acid (4.6%), arachidonic acid (0.4%), and lignoceric acid (0.04%). The medicinal efficacy of *Sesamum indicum* is widely known. In particular, based on records, black sesame seed has mild properties, tastes sweet, is not poisonous, supplements energy, makes fat, strengthens the bone marrow and brain marrow, strengthens the tendons and bones, relaxes the five intestines, supplements the bone marrow, replenishes the vital essence, makes a person live longer and makes a person's face look younger, and the oil of black sesame seed increases the number of platelets in the blood, causing the blood to coagulate quickly.

*Quercus robur*, also known as English oak, is mainly found in Europe. The tree grows in the wild and may grow from 4 m to 12 m in circumference. Leaves begin to grow in April or May, and fall in October or November. *Quercus robur* leaves are slightly smaller than other oak leaves, and are distinguished from other oaks by the short petioles and small rounded lobes. *Quercus robur* is a very long-lived tree, and may live for about 1000 years. The fruit is a thin and long acorn, and in early spring, acorns are produced and grown almost simultaneously with the leaves.

*Houttuynia cordata* is a perennial plant of the family Saururaceae, and the above-ground part of *Houttuynia cordata* Thunb appears during the flowering period in Korea. As a perennial traditional medicinal plant, it has been used as a disinfectant, a diuretic, an antipyretic and the like for a long period of time in countries such as Korea, Japan and China. Moreover, the diuretic, detoxification, cardiotonic, antipyretic, drainage, and anticancer effects thereof are known.

*Cirsium japonicum* is thistle belonging to the family Compositae, and is a whole plant related to other plants in the same genus. The main active ingredient thereof is a flavonoid compound. Through pharmacological research, it has been found to have relatively strong inhibitory activity against *Staphylococcus aureus*, and a hot-water extract of roots or a distillate of whole plant is able to exhibit an inhibitory effect against human interactive *bacillus*, and also a distinct inhibitory effect against *Pseudomonas aeruginosa*, modified *bacillus*, simple zoster virus, etc. The *Cirsium japonicum* extract used in the present disclosure is only extracts extracted from the flowers, leaves or stems of *Cirsium japonicum*.

*Thuja orientalis* is an evergreen arboreous tree of the family Cupressaceae of the order Coniferales of the subclass Coniferophytae of gymnosperms, and is known to be effective for reducing hematochezia, hematuria, epistaxis (nosebleed), hematemesis, hemoptysis, bloody stool, uterine hemorrhaging, cough, sputum, asthma, hair loss, seborrheic dermatitis, hypotension, erysipelas (acute infectious disease caused by *Streptococcus* or *Staphylococcus aureus* entering an injured site of the skin or mucous membrane), metrorrhagia (bleeding due to uterine hemorrhage from the female genital tract), tuberculous hemorrhoid (a type of hemorrhoid characterized by clear, bright reddish bleeding before defecation), scalding burn (burning limbs in boiling water or hot oil), bloody diarrhea (a type of dysentery, stool with blood, or blood without stool), mumps (epidemic parotitis), toxic swelling (dispersion of poison caused by swelling), etc. In the present disclosure, an extract extracted from *Thuja orientalis* sap or *Thuja orientalis* leaves is used.

A method of extracting the natural substance serving as the active ingredient of the present disclosure is described below.

The extract of the substance used as the active ingredient of the present disclosure includes an extract that may be obtained through a typical extraction process known in the art. For example, the extract may be obtained using, as an extraction solvent, water, anhydrous or hydrous lower alcohols having 1-4 carbon atoms (methanol, ethanol, propanol, butanol, etc.), acetone, ethyl acetate, chloroform, butyl acetate, or 1,3-butylene glycol, etc., which may be used alone or in mixtures thereof.

Preferably, the extract of the present disclosure is obtained using water, ethanol, or a mixed solvent of ethanol and water as an extraction solvent. Meanwhile, it is possible to obtain an extract of the present disclosure that exhibits substantially the same effect even when using other extraction solvents, in addition to the extraction solvent described above, as will be apparent to those skilled in the art. Moreover, the extract of the present disclosure includes an extract obtained through any typical purification process, in addition to the extract using the extraction solvent described above.

In addition, the present disclosure pertains to a cosmetic composition for preventing and ameliorating acne symptoms including the composition for preventing, ameliorating or treating acne symptoms described above.

The cosmetic composition may be in any one form selected from the group consisting of a skin lotion, a nourishing lotion, a gel, a water-soluble liquid, a milk lotion, a nourishing cream, a massage cream, an essence, an eye cream, an oil-in-water (O/W) or water-in-oil (W/O) emulsion, an oil dispersion in an aqueous phase using globules, an ointment, a cleansing cream, a cleansing foam, a cleansing water, a pack or body oil, an oil-in-water or water-in-oil makeup base, a foundation, a skin cover, a face powder, and a two-way cake.

A better understanding of the composition for preventing, ameliorating or treating acne symptoms using natural extracts as active ingredients according to the present disclosure may be obtained through the following examples with reference to the accompanying drawings so that the present disclosure can be easily performed by those skilled in the art.

[Experimental Materials and Experimental Methods]
Preparation Example of Extract
(1) Preparation of *Sesamum indicum* Seed Extract
500 g of *Sesamum indicum* L. was pulverized and extracted three times with 1 l of n-hexane, thus obtaining 250 g of a defatted *Sesamum indicum* powder. The defatted *Sesamum indicum* powder was extracted under reflux with 1 l of 80% (v/v) ethanol aqueous solution at room temperature for 24 hours, and the filtrate and the residue extract were combined, filtered, and concentrated under reduced pressure. After filtration and concentration under reduced pressure, all extracts were lyophilized, powdered, and used in the experiment.

(2) Preparation of *Quercus robur* Bark Extract
Dry *Quercus robur* bark (using the bark of the stem) was finely cut, and 80 vol % ethanol per 500 g of raw material was added in an amount corresponding to 10 times the volume of the raw material of *Quercus robur* bark, followed by extraction under reflux for 24 hours at room temperature, after which the filtrate and the residue extract were combined, filtered, and then concentrated under reduced pressure. After filtration and concentration under reduced pressure, all extracts were lyophilized, powdered, and used in the experiment.

(3) Preparation of *Houttuynia cordata* Extract
An extract was prepared in the same manner as in the procedure for preparing the *Quercus robur* bark extract, with the exception that *Houttuynia cordata* was used.

(4) Preparation of *Cirsium japonicum* Extract
An extract was prepared in the same manner as in the procedure for preparing the *Quercus robur* bark extract, with the exception that *Cirsium japonicum* leaves were used.

(5) Preparation of *Thuja orientalis* Extract
An extract was prepared in the same manner as in the procedure for preparing the *Quercus robur* bark extract, with the exception that *Thuja orientalis* leaves were used.

Preparation of Composition for Preventing, Ameliorating or Treating Acne Symptoms
In order to compare the effects of natural plant extracts depending on the combination of the extracts of the present disclosure, mixtures of extracts obtained through possible combinations of the extracts prepared above were prepared using the components in the amounts shown in Tables 1 and 2 below.

TABLE 1

| Composition | Sesamum indicum seed extract (parts by weight) | Quercus robur bark extract (parts by weight) | Houttuynia cordata extract (parts by weight) | Cirsium japonicum extract (parts by weight) | Thuja orientalis extract (parts by weight) | Purified water (parts by weight) |
|---|---|---|---|---|---|---|
| Example 1 | 2.25 | 2.25 | 2.25 | 2.25 | — | 100 |
| Example 2 | 2.25 | 2.25 | 2.25 | — | 2.25 | 100 |
| Example 3 | 1.8 | 1.8 | 1.8 | 1.8 | 1.8 | 100 |

For reference, the composition for preventing, ameliorating or treating acne symptoms of the present disclosure as shown in Table 1 may include 0.05 to 5 parts by weight of each extract based on 100 parts by weight of purified water.

TABLE 2

| Composition | Sesamum indicum seed extract (parts by weight) | Quercus robur bark extract (parts by weight) | Houttuynia cordata extract (parts by weight) | Cirsium japonicum extract (parts by weight) | Thuja orientalis extract (parts by weight) | Purified water (parts by weight) |
|---|---|---|---|---|---|---|
| Comparative Example 1 | 9 | — | — | — | — | 100 |
| Comparative Example 2 | — | 9 | — | — | — | 100 |

TABLE 2-continued

| Composition | Sesamum indicum seed extract (parts by weight) | Quercus robur bark extract (parts by weight) | Houttuynia cordata extract (parts by weight) | Cirsium japonicum extract (parts by weight) | Thuja orientalis extract (parts by weight) | Purified water (parts by weight) |
|---|---|---|---|---|---|---|
| Comparative Example 3 | — | — | 9 | — | — | 100 |
| Comparative Example 4 | — | — | — | 9 | — | 100 |
| Comparative Example 5 | — | — | — | — | 9 | 100 |
| Comparative Example 6 | 4.5 | 4.5 | — | — | — | 100 |
| Comparative Example 7 | 4.5 | — | 4.5 | — | — | 100 |
| Comparative Example 8 | 4.5 | — | — | 4.5 | — | 100 |
| Comparative Example 9 | 4.5 | — | — | — | 4.5 | 100 |
| Comparative Example 10 | — | 4.5 | 4.5 | — | — | 100 |
| Comparative Example 11 | — | 4.5 | — | 4.5 | — | 100 |
| Comparative Example 12 | — | 4.5 | — | — | 4.5 | 100 |
| Comparative Example 13 | — | — | 4.5 | 4.5 | — | 100 |
| Comparative Example 14 | 4.5 | 4.5 | — | — | — | 100 |
| Comparative Example 15 | — | — | — | 4.5 | 4.5 | 100 |
| Comparative Example 16 | 3 | 3 | 3 | — | — | 100 |
| Comparative Example 17 | 3 | 3 | — | 3 | — | 100 |
| Comparative Example 18 | 3 | 3 | — | — | 3 | 100 |
| Comparative Example 19 | 3 | — | 3 | 3 | — | 100 |
| Comparative Example 20 | 3 | — | 3 | — | 3 | 100 |
| Comparative Example 21 | 3 | — | — | 3 | 3 | 100 |
| Comparative Example 22 | — | 3 | 3 | 3 | — | 100 |
| Comparative Example 23 | — | 3 | 3 | — | 3 | 100 |
| Comparative Example 24 | — | 3 | — | 3 | 3 | 100 |
| Comparative Example 25 | — | — | 3 | 3 | 3 | 100 |
| Comparative Example 26 | 2.25 | — | 2.25 | 2.25 | 2.25 | 100 |
| Comparative Example 27 | — | 2.25 | 2.25 | 2.25 | 2.25 | 100 |
| Comparative Example 28 | 2.25 | 2.25 | — | 2.25 | 2.25 | 100 |

Evaluation of Effect of Composition of the Present Disclosure

<Experimental Example 1> Measurement of Antibacterial Activity (1) Usage Strain, Medium, and Culture Conditions The strain used to confirm the ability to reduce acne in the present experiment was *C. acnes* KCOM 1861 (=ChDC B594), which is the stain causative of acne. A reinforced clostridial (RC) medium (Merck, Germany) was used as the culture medium for acne bacteria, and *C. acnes* KCOM 1861 (=ChDC B594) was activated 3 days before the experiment while being stored at 4° C. The bacteria were inoculated in the culture medium, sealed in an anaerobic jar using a gas pack system (Merck Anaerocult gas pack system, Germany), and then subjected to anaerobic culture for 3 days in an incubator at 37° C.

The antibacterial activity of the extracts according to the present disclosure was measured as described below using an agar well diffusion assay (Ansari et al., 2012). More specifically, a well having a diameter of 10 mm was pierced with a cork borer in an NA medium coated with the acne-causing strain, 100 j of the composition of each of Examples 1 to 3 and Comparative Examples 1 to 28 was added thereto, and a petri dish was wrapped with a parafilm, followed by culture (30° C., 24 hours), after which the diameter of inhibition was measured.

[Experiment Result]
Result of Measurement of Antibacterial Activity (Agar Well Diffusion Assay)

The results of measurement of the antibacterial activity of the compositions of Examples 1 to 3 and Comparative Examples 1 to 28 according to Experimental Example 1 are shown in Table 3 below.

TABLE 3

| Composition | Diameter of inhibition (mm) |
|---|---|
| Example 1 | 14.16 ± 0.23 |
| Example 2 | 16.86 ± 0.34 |
| Example 3 | 20.1 ± 0.45 |
| Comparative Example 1 | 7.14 ± 0.22 |
| Comparative Example 2 | 4.47 ± 0.38 |
| Comparative Example 3 | 7.14 ± 0.56 |
| Comparative Example 4 | 5.23 ± 0.38 |
| Comparative Example 5 | 7.38 ± 0.53 |
| Comparative Example 6 | 6.06 ± 0.24 |
| Comparative Example 7 | 6.9 ± 0.22 |
| Comparative Example 8 | 6.48 ± 0.34 |
| Comparative Example 9 | 7.26 ± 0.56 |
| Comparative Example 10 | 5.97 ± 0.20 |
| Comparative Example 11 | 5.06 ± 0.48 |
| Comparative Example 12 | 6.12 ± 0.42 |
| Comparative Example 13 | 6.3 ± 0.33 |
| Comparative Example 14 | 6.84 ± 0.19 |
| Comparative Example 15 | 6.54 ± 0.65 |
| Comparative Example 16 | 8.28 ± 0.44 |
| Comparative Example 17 | 5.79 ± 0.22 |
| Comparative Example 18 | 6.12 ± 0.34 |
| Comparative Example 19 | 6.48 ± 0.26 |
| ComparativeExample 20 | 7.62 ± 0.24 |
| Comparative Example 21 | 7.44 ± 0.48 |
| Comparative Example 22 | 6.78 ± 0.56 |
| Comparative Example 23 | 6.9 ± 0.38 |
| Comparative Example 24 | 7.62 ± 0.16 |
| Comparative Example 25 | 7.56 ± 0.33 |
| Comparative Example 26 | 9.48 ± 0.65 |
| Comparative Example 27 | 8.34 ± 0.53 |
| Comparative Example 28 | 9.9 ± 0.58 |

As is apparent from Table 3, each of the *Sesamum indicum* seed extract, the *Quercus robur* bark extract, the *Houttuynia cordata* extract, the *Cirsium japonicum* extract, and the *Thuja orientalis* extract was evaluated to exhibit antibacterial activity against *C. acnes* KCOM 1861 (=ChDC B594), which is the strain causative of acne (Comparative Examples 1 to 5), and was measured to form an inhibition zone of about 4.5 mm to 7.4 mm.

In Comparative Examples 6 to 25, the compositions including combinations of two or three extracts among the five extracts formed inhibition zones of about 5.1 mm to 8.3 mm against *C. acnes* KCOM 1861 (=ChDC B594). As described above, when combining two or three extracts among the five natural substance extracts, such as the *Sesamum indicum* seed extract, the *Quercus robur* bark extract, the *Houttuynia cordata* extract, the *Cirsium japonicum* extract and the *Thuja orientalis* extract, the effects thereof were found to vary slightly depending on the type of combination but to be similar to the simple sum of the effects of individual natural substance extracts.

Even in the four extracts, in which any one of the *Sesamum indicum* seed extract, the *Quercus robur* bark extract, and the *Houttuynia cordata* extract was omitted, the antibacterial activity increased (maximum inhibition zone: 9.9±0.58 mm), but the extent thereof was not great. However, as shown in the experimental results of Examples 1 and 2, when the base composition containing the *Sesamum indicum* seed extract, the *Quercus robur* bark extract, and the *Houttuynia cordata* extract was further combined with the *Cirsium japonicum* extract or the *Thuja orientalis* extract, the minimum inhibition zone was greatly enlarged. Specifically, based on the result in which the inhibition zone of the composition containing only the *Sesamum indicum* seed extract, the *Quercus robur* bark extract and the *Houttuynia cordata* extract was 8.28±0.44 mm, when the *Sesamum indicum* seed extract, the *Quercus robur* bark extract and the *Houttuynia cordata* extract were further combined with the *Cirsium japonicum* extract or the *Thuja orientalis* extract according to Examples of the present disclosure, the minimum inhibition zone diameter was increased by at least 5.8 mm, which remarkably exceeds the extent of improvement in antibacterial activity that would typically be expected from a simple combination of the natural substance extracts described above.

In addition, as shown in the experimental results of Example 3 using the composition containing all of the *Sesamum indicum* seed extract, the *Quercus robur* bark extract, the *Houttuynia cordata* extract, the *Cirsium japonicum* extract, and the *Thuja orientalis* extract, the size of the inhibition zone against *C. acnes* KCOM 1861 (=ChDC B594), which is the strain causative of acne, was 20.1±0.45 mm. When all five natural substance extracts were combined, the strongest antibacterial activity against *C. acnes* KCOM 1861 (=ChDC B594), which is the strain causative of acne, was exhibited by virtue of the synergistic effect due to the interactions between the natural substance extracts.

Therefore, it can be concluded that the natural extracts according to the present disclosure can be effectively used for a composition for preventing, ameliorating or treating acne symptoms.

Although the preferred embodiments of the present disclosure have been disclosed for illustrative purposes, those skilled in the art will appreciate that various modifications and equivalents are possible, without departing from the scope and spirit of the disclosure as disclosed in the accompanying claims. Therefore, the scope of the present disclosure should be determined based on the accompanying claims.

What is claimed is:

1. An emulsion for treating acne symptoms on the skin of a human consisting essentially of therapeutically effective amounts of a *Sesamum indicum* seed extract, a *Quercus robur* bark extract, a *Houttuynia cordata* extract, a *Cirsium japonicum* extract and a *Thuja orientalis* extract.

2. The emulsion of claim 1, wherein the *Cirsium japonicum* extract is an extract extracted from at least one of a flower, leaf, and stem of *Cirsium japonicum*.

3. The emulsion of claim 1, wherein the *Thuja orientalis* extract is an extract extracted from at least one of *Thuja orientalis* sap and a *Thuja orientalis* leaf.

4. The emulsion claim 1, wherein each of the *Sesamum indicum* seed extract, the *Quercus robur* bark extract, the *Houttuynia cordata* extract, the *Cirsium japonicum* extract, and the *Thuja orientalis* extract is used in an amount of 0.05 to 5 parts by weight based on 100 parts by weight of purified water.

5. The emulsion of claim 1, further consisting essentially of purified water, vitamin C, royal jelly, glycerin, ethanol, and xanthan gum, wherein each of the vitamin C, royal jelly, glycerin, ethanol, and xanthan gum is used in an amount of 0.01 to 15 parts by weight based on 100 parts by weight of the purified water.

6. The emulsion of claim 1, wherein the emulsion is in a form of a gel or a liquid.

* * * * *